(12) United States Patent
Lam et al.

(10) Patent No.: US 10,793,866 B2
(45) Date of Patent: Oct. 6, 2020

(54) EDIBLE VACCINES EXPRESSED IN YEAST FOR PREVENTING AND TREATING INFECTIOUS DISEASES, INCLUDING HEPATITIS B, IN HUMANS

(71) Applicants: Dominic Man-Kit Lam, Hong Kong (HK); Olivia Yee-Yee Lam, Los Angeles, CA (US); Han Lei, Hong Kong (HK)

(72) Inventors: Dominic Man-Kit Lam, Hong Kong (HK); Olivia Yee-Yee Lam, Los Angeles, CA (US); Han Lei, Hong Kong (HK)

(73) Assignee: DrD LifeSciences Group Limited, Wan Chai (HK)

(*) Notice: Subject to any disclaimer, the term of this patent is extended or adjusted under 35 U.S.C. 154(b) by 50 days.

(21) Appl. No.: 15/937,622

(22) Filed: Mar. 27, 2018

(65) Prior Publication Data

US 2019/0300887 A1    Oct. 3, 2019

(51) Int. Cl.
| | | |
|---|---|---|
| *A61K 38/00* | (2006.01) | |
| *A61K 39/00* | (2006.01) | |
| *C07K 14/00* | (2006.01) | |
| *A61K 38/16* | (2006.01) | |
| *A61K 39/12* | (2006.01) | |
| *C12N 15/81* | (2006.01) | |
| *G01N 33/576* | (2006.01) | |
| *A61K 39/29* | (2006.01) | |
| *A61K 9/48* | (2006.01) | |
| *A61K 9/00* | (2006.01) | |

(52) U.S. Cl.
CPC ............ *C12N 15/81* (2013.01); *A61K 9/0056* (2013.01); *A61K 9/48* (2013.01); *A61K 39/292* (2013.01); *G01N 33/5764* (2013.01); *A61K 2039/523* (2013.01); *A61K 2039/54* (2013.01); *C12N 2800/102* (2013.01)

(58) Field of Classification Search
CPC .... A61K 38/00; C07K 14/505; C07K 14/005; C07K 2319/00; C07K 9/00
See application file for complete search history.

*Primary Examiner* — Barry A Chestnut

(57) ABSTRACT

In the invention described here, the approach is to formulate an edible vaccine based on N-terminal yeast surface display expression platform that producing *S.cerevisiae* EBY100/pYD5-preS2/S(adw) and *S.cerevisiae* EBY100/pYD5-preS2/S(adr) for protecting and treating human against hepatitis B virus (HBV) infection, suggesting that yeast surface display expression system expressing HBsAg antigen has potential as a prophylactic treatment for HBV in human via oral vaccination. The technology developed in this patent application can also be used to produce edible (oral) vaccines for preventing and treating other infectious diseases in human.

11 Claims, No Drawings

Specification includes a Sequence Listing.

SEQUENCE LISTING

```
<160> NUMBER OF SEQ ID NOS: 2

<210> SEQ ID NO 1
<211> LENGTH: 846
<212> TYPE: DNA
<213> ORGANISM: Hepatitis B virus

<400> SEQUENCE: 1
atgcagtgga attccactgc cttccaccaa gctctgcagg atcccagagt caggggcctg      60
tattttcctg ctggtggctc cagttcagga acagtaaacc ctgctccgaa tattgcctct     120
cacatctcgt caatctccgc aaggactggg gaccctgtta cgaacatgga gaacatcaca     180
```

```
tcaggattcc taggacccct gctcgtgtta caggcggggt ttttcttgtt gacaagaatc      240
ctcacaatac cgcagagtct agactcgtgg tggacttctc tcaattttct aggggggatca     300 cccgtgtgtc ttggccaaaa ttcgcagtcc ccaacctcca atcactcacc aacctcctgt      360
cctccaattt gtcctggtta tcgctggatg tgtctgcggc gttttatcat attcctcttc      420
atcctgctgc tatgcctcat cttcttattg gttcttctgg attatcaagg tatgttgccc      480
gtttgtcctc taattccagg atcaacaaca accagtacgg gaccatgcaa aacctgcacg      540
actcctgctc aaggcaactc tatgtttccc tcatgttgct gtacaaaacc tacggatgga     600
aattgcacct gtattcccat cccatcgtcc ttggctttcg caaaatacct atgggagtgg     660
gcctcagtcc gtttctcttg gctcagttta ctagtgccat tgttcagtg gttcgtaggg      720 ctttcccca ctgtttggct ttcagctata tggatgatgt ggtatggggg gccaagtctg     780
tacagcatcg tgagtccctt tataccgctg ttaccaattt tctttttgtct ctgggtatac    840 atttaa                                                                 846

<210> SEQ ID NO 2
<211> LENGTH: 837
<212> TYPE: DNA
<213> ORGANISM: Hepatitis B virus

<400> SEQUENCE: 2
atgtccacaa cattccacca agctctgcta gaccccagag tgaggggcct atactttcct      60
gctggtggct ccagttccgg aacagtaaac cctgttccga ctactgcctc acccatatcg     120
tcaatcttct cgaggactgg gcaccctgca ccgaacatgg agaacacaac atcaggattc     180
ctaggacccc tgctcgtgtt acaggcgggg ttttcttgt tgacaagaat cctcacaata     240
ccacagagtc tagactcgtg gtggacttct ctcaattttc taggggggagc acccacgtgt    300 cctggccaaa attcgcagtc cccaacctgc aatcactcac caacctcttg tcctccaatt    360
tgtcctgcgt atcgctggat gtgtctgcgg cgttttatca tattcctctt catcctgctg    420
ctatgcctca tcttcttgtt ggttcttctg gactaccaag gtatgttgcc cgtttgtcct    480
ctacttccag gaacatcaac taccagcacg ggaccatgca agacctgcac gactcctgct    540
caaggaacct ctatgtttcc ctcttgttgc tgtacaaaac cttcggacgg aaactgcact    600
tgtattccca tcccatcatc ctgggctttc gcaagattcc tatgggagtg ggcctcagtc    660
cgtttctcct ggctcagttt actagtgcca tttgttcagt ggttcgtagg gctttccccc     720
actgtttggc tttcagttat atggatgatg tggtattggg ggccaagtct gtacaacatc     780
ttgagtccct ttttacctct attaccaatt ttcttttgtc tttgggtata catttaa        837
```

EDIBLE VACCINES EXPRESSED IN YEAST FOR PREVENTING AND TREATING INFECTIOUS DISEASES, INCLUDING HEPATITIS B, IN HUMANS

FIELD OF THE INVENTION

The present invention is for the composition of an edible vaccine based on yeast surface display expressions for creating an edible vaccine that prevents and treats infections in humans, protecting humans from being infected with hepatitis B virus (HBV). The present invention comprises mainly a N-terminal yeast surface expression system and oral vaccination in humans.

BACKGROUND OF THE INVENTION

Hepatitis B virus (HBV) causes most cases of hepatitis in China and the world. Although the world now has the tools to prevent hepatitis B, there is no cure for the millions of people already infected. In other word, currently available HBV vaccine has a role in preventing health human from HBV infection, but there is no cure role. Further, conventional immune route such as injection is not suitable for the low-income people in the third world. Unfortunately, there are no commercial HBV vaccine with oral administration. The purpose of this invention is to establish yeast surface display platform to deliver preventive and therapeutic HBV vaccines by oral administration.

The concept of edible vaccine was proposed by Prof. Dominic Lam and executed by him and his colleagues in early 1990s who first reported the expression of hepatitis B virus surface antigen (HBsAg) in tomato. Edible vaccines will be more acceptable because of its oral rather than injectable route of application. In contrast, producing the vaccines in plants could reduce the cost to less than a penny per dose, and simple fast food processing like drying and grinding could create non-perishable preparations without refrigeration. Further, Prof. Dominic Lam and his research team also focus on *Lactococcus* and yeast based vaccines which are used to prevent avian influenza infection.

Yeast surface display technology has been extensively developed for application in preventing virus affection. Recently, *Saccharomyces cerevisiae* (*S.cerevisiae*) surface display was used to develop H5N1 and Zika virus vaccines. Currently, *P.pastoris* secretion system has been designed to express HBsAg of HBV, these commercial HBV vaccines have been used for preventing HBV infection. Unfortunately *P.pastoris* secretion system would not be used to produce edible HBV vaccines. Importantly, there are no attempts to develop preventive and therapeutic HBV vaccines with oral administration using *S.cerevisiae* display system which is more efficient than *P.pastoris* for producing HBV vaccines.

Collectively, we propose this invention that *S.cerevisiae* surface display system can be used to develop preventive and therapeutic HBV vaccines. To address this invention, HBsAg of HBV adw and adr genotypes are investigated by *S.cerevisiae* N-terminal surface display platforms.

Although the mechanism underlying the interaction between HBV and host cells remain unknown, adw preS2/S (309 kDa) and adr preS2/S (30.8 kDa) are generally considered major surface antigen proteins of HBV, which are involved in the infection process as an attachment protein. This is the primary reason why preS2/S protein has been used as an effective candidate target for potential HBV vaccines development.

Vaccination is currently the only method that can effectively stop the spread of HBV in humans. Conventional platform based on *P.pastoris* secretion system for HBV vaccine shows limits for producing edible vaccines. In the present invention, we describe a new type of potent edible HBV vaccine based on yeast surface display system.

The present invention can provide an effective way to protect human from HBV infection and cure already affected. It may also be used to produce edible vaccines for preventing and treating other infectious diseases in humans.

SUMMARY OF THE INVENTION

The present invention is about an edible vaccine for preventing and treating HBV infection in humans. The present invention describes that a N-terminal display plasmid, pYD5, to display preS2/S (adw) or preS2/S (adr) protein on the surface of *S.cerevisiae* EBY100 and detected by Western blotting, immunofluorescence and flow cytometric assay. The recombinant yeast after lyophilization is encapsulated by enteric capsule, followed by ELISA detecting antibody responses. The present invention suggests that yeast display expression system can be developed for edible HBV vaccines for preventing and treating HBV infection.

The present invention contains 3 major parts: (i) the construction of recombinant yeast, (ii) the recombinant yeast is lyophilized and then encapsulated by enteric capsule, (iii) antibody responses from the vaccinated humans is detected by ELISA.

DETAILED DESCRIPTION OF INVENTION

Construction of HBsAg Antigen Surface-Displayed Yeast Vaccines

The preS2/S gene (Gene accession No. U87732.1, 846 bp) from HBV adw subtype will be PCR-amplified using specific primers and subcloned into pYD5 in-frame with the endogenous Aga2p signal peptide sequence. The resultant shuttle plasmid pYD5-preS2/S will be transformed into *E. coli* DH5α. The plasmid pYD5-preS2/S will then be extracted from *E. coli*, purified and electroporated into competent *S.cerevisiae* EBY100 after being linearized. Recombinant yeast transformants will be plated on selective minimal dextrose plates containing amino acids (0.67% yeast nitrogen base without amino acids (YNB), 2% glucose, 0.01% leucine, 2% agar, and 1M sorbitol). Trp$^+$ transformants will be selected after 3 days of growth on the selective minimal dextrose plates.

The positive colonies are confirmed by genomic PCR. Recombinant *S. cerevisiae* EBY100/pYD5-preS2/S(adw) is cultured in YNB-CAA-Glu (0.67% YNB, 0.5 casamino acids, 2% Glucose) and induced in YNB-CAA-Gal (0.67% YNB, 0.5 casamino acids, 2% Galactose, 13.61 g/L Na$_2$HPO$_4$, 7.48 g/L NaH$_2$PO$_4$ and 5 g/L casamino acids) at 20° C. with shaking (250 rpm) for inducing VP28 surface display. *S.cerevisiae* EBY 100 carrying pYD5 plasmid (*S.cerevisiae* EBY 100/pYD5) is served as a negative control for all the subsequent tests.

One more type of HBV vaccine will be constructed in this section:

*S.cerevisiae* EBY100/pYD5-preS2/S(adr)—preS2/S surface displayed yeast vaccine.

Note: The preS2/S gene (Gene accession No. AF036239, 834 bp) from HBV adr subtype.

Determining the Functional Display of HBsAg Antigen on Yeast Surface

This experiment is designed to validate the functional display of the preS2/S antigen on yeast surface.

Western Blotting

1 $OD_{600}$ (1 $OD_{600}$≈$10^7$ cells) equivalent recombinant yeast will be collected at different time point post inducement with 2% galactose. The samples are washed three times with 500 µl of PBS, re-suspended in 50 µl of 6×SDS loading buffer (Bio-Rad, Hercules, Calif.), and boiled for 10 min. The surface presented preS2/S will be extracted by heating 1 $OD_{600}$ of *S.cerevisiae* EBY100/pYD5-preS2/S (adw) pellets at 95° C. in a Bromophenol blue sample buffer supplemented with 5%-ME for 5 min. The samples were then resolved on a 4-15% SDS-PAGE gel (Bio-Rad), and transferred to 0.45 µm nitrocellulose membranes (Bio-Rad). After blocking with 5% non-fat milk at room temperature for 2 h, the membrane will be incubated with polyclonal horse anti-Hepatitis B Virus surface antigen (Abeam) as primary antibody (1:500 diluted). After incubated overnight at 4° C. and washed three times using PBS buffer, the membranes will be reacted to the secondary antibodies, horseradish peroxidase (HRP)-conjugated goat anti-horse IgG (1:5,000 diluted) (Sigma-Aldrich Co., St. Louis, Mo.) for 1 hour at room temperature. The signal will be generated using West Pico chemiluminescent substrates (Thermo Fisher Scientific Inc., Rockford, Ill.) and detected using a ChemiDoc XRS System (Bio-Rad).

Glycosylation Analysis of Yeast Surface Displayed PreS2/S

PNGase F is obtained from New England Labs (Beverly, Mass.). Recombinant *S. cerevisiae* EBY100/pYD5-preS2/S (adw) will be cultured at 30° C. in YNB-CAA-Glu overnight and then induced at 20° C. in YNB-CAA-Gal for 72 hours. 1 $OD_{600}$ equivalent cells will be collected, centrifuged, and washed once in a PBS buffer. Cell pellets were denatured at 100° C. for 10 min in a denaturing buffer included in the PNGase F reagent. A portion of 1 µL of PNGase F (5,000 U) will be added to the denatured protein solution, followed by incubation at 37° C. for 1 hour according to the manufacturer's instruction. The treated samples will then be subjected to Western blotting analysis.

Immunofluorescence Microscopy

To determine preS2/S display on yeast surface, recombinant *S. cerevisiae* EBY100/pYD5-preS2/S(adw) will be collected in a 24-hour interval over a 72-hour time period after induction with galactose (2%). $1OD_{600}$ equivalent recombinant yeast will be collected and blocked with 5% non-fat milk in PBS for 1 hour, and incubated with polyclonal horse anti-Hepatitis B Virus surface antigen (1:500 diluted) at 4° C. for 1 hour. After washing with PBS, the samples will be incubated with goat anti-horse IgG FITC conjugates (Sigma) (1:5,000 diluted) at room temperature for 1 h. The samples will be kept in dark until use. The FITC labeled yeast will be examined under an inverted phase contrast fluorescence microscope.

Flow Cytometric Assay

After inducement with galactose (2%), 1 $OD_{600}$ equivalent recombinant yeasts will be collected over a 72-hour time period, with a 24-hour interval, as described above. The cell samples will be washed three times with sterile PBS containing 1% bovine serum albumin (BSA) and incubated with polyclonal horse anti-Hepatitis B Virus surface antigen (1:500 diluted) at 4° C. for 1 hour, followed by reacting with FITC-conjugated goat anti-horse IgG (1:5,000) at 4° C. for 30 min. The cell samples will be re-suspended in 500 µL of sterile PBS and will be subject to flow cytometric analysis using a BD FACS Aira III (BD Bioscience, San Jose, Calif.). *S.cerevisiae* EBY100/pYD5 served as a negative control for the assay. These data will be used to ascertain which time point will be the best for collecting yeast vaccines that present the highest level of preS2/S on their surface.

Note: The similar methods are used to determine the functional display for the following *S.cerevisiae* EBY100/pYD5-preS2/S(adr).

Lyophilization and Encapsulation

Recombinant yeast is lyophilized and then encapsulated by enteric capsule.

Optimization of Oral Immunization

HBV transgentic mice is used in this invention. A batch of mice was divided into five groups and 10 mice per group were selected. Each mouse orally vaccinated with one capsule containing recombinant yeast feed continuously for 3 days, boosted at day 15-18. The oral vaccination experiments were repeated three times.

ELISA Assay

Tenth day after the final vaccination, blood sample was isolated from the vaccinated mice.

Antibody responses of serum IgG was determined by enzyme-linked immunosorbent assay (ELISA) using recombinant HBaAg protein (2 µg/ml) as a coating antigen as described previously. Optical density (OD) was measured at 405 nm using ELI SA plate reader. The IgG titer was determined to be the lowest dilution with an OD greater than the mean OD of naïve controls plus 2 standard deviations.

Based on these results, we can evaluate and determine the strength and degree of immune protection that can be provided by the yeast vaccines. Further, we can determine which vaccine provides the complete immune protection of human from HBV infection.

What is claimed is:

1. A composition for preventing and treating hepatitis B virus (HBV) infection in humans comprising a yeast expression plasmid, pYD5, for N-terminal surface display, wherein the recombinant plasmid contains SEQ ID NO: 1 or SEQ ID NO:2.

2. The composition of claim 1, wherein yeast that includes recombinant plasmid.

3. The composition of claim 2, wherein the said yeast is S.cerevisiae EBY100.

4. The composition according to claim 2 or 3, wherein the said recombinant yeast can be used for developing vaccine for preventing HBV infection.

5. The composition of claim 4, wherein the said vaccine is orally administrated.

6. The composition according to claim 2 or 3, wherein the HBV vaccine formulation comprises recombinant yeast plus additional component.

7. The composition of claim 6, wherein the said formulation is orally administrated.

8. A composition as claimed in claim 7, antibody responses from the vaccinated mice are detected by ELISA.

9. A method for constructing recombinant yeast comprising the step of applying the composition in claim 1 or 2.

10. A method for delivering recombinant yeast comprising the step of applying the composition in claim 5, 6 or 7.

11. A method for evaluating the protective efficiency of recombinant yeast comprising the step of applying the composition in claim 8.

* * * * *